United States Patent
Johnston et al.

(10) Patent No.: US 9,309,298 B2
(45) Date of Patent: Apr. 12, 2016

(54) ANTI-BACTERIAL POLYPEPTIDES AND PATHOGEN SPECIFIC SYNTHETIC ANTIBODIES

(71) Applicants: Stephen Johnston, Tempe, AZ (US); Valeriy Domenyuk, Tempe, AZ (US); Chris Diehnelt, Chandler, AZ (US)

(72) Inventors: Stephen Johnston, Tempe, AZ (US); Valeriy Domenyuk, Tempe, AZ (US); Chris Diehnelt, Chandler, AZ (US)

(73) Assignee: Arizona Board of Regents, a Body Corporate of the State of Arizona, Acting for and on Behalf of Arizona State University, Scottsdale, AZ (US)

( * ) Notice: Subject to any disclaimer, the term of this patent is extended or adjusted under 35 U.S.C. 154(b) by 38 days.

(21) Appl. No.: 14/355,839

(22) PCT Filed: Nov. 1, 2012

(86) PCT No.: PCT/US2012/063029
§ 371 (c)(1),
(2) Date: May 1, 2014

(87) PCT Pub. No.: WO2013/067160
PCT Pub. Date: May 10, 2013

(65) Prior Publication Data
US 2014/0296132 A1    Oct. 2, 2014

Related U.S. Application Data

(60) Provisional application No. 61/554,593, filed on Nov. 2, 2011.

(51) Int. Cl.
C07K 14/435    (2006.01)
C07K 7/08      (2006.01)
A61K 38/00     (2006.01)

(52) U.S. Cl.
CPC ............... *C07K 14/435* (2013.01); *C07K 7/08* (2013.01); *A61K 38/00* (2013.01); *C07K 2319/33* (2013.01)

(58) Field of Classification Search
CPC .. A61K 38/00; C07K 14/435; C07K 2319/33; C07K 7/08
See application file for complete search history.

(56) References Cited

U.S. PATENT DOCUMENTS

2011/0136727 A1    6/2011    Svarovsky

FOREIGN PATENT DOCUMENTS

| WO | WO2008048970 A2 | 4/2008 |
| WO | WO2010111299 A2 | 9/2010 |
| WO | WO2011029008 A2 | 3/2011 |

OTHER PUBLICATIONS

Johnston, Synthetic and Systems Biology Forum on Microbial Threats, Biodesign Institute at Arizona State University, 30 pages (Mar. 14, 2011); also available at http://iom.nationalacademies.org/~/media/Files/Activity%20Files/PublicHealth/MicrobialThreats/2011-MAR-14/Johnston.pdf (last visited Feb. 8, 2016).*
Diehnelt et al., (2010). "Discovery of high-affinity protein binding ligands-backwards." PLoS One 5(5).
Giuliani et al., (2007). "Antimicrobial peptides: an overview of a promising class of therapeutics." CEJB 2(1): 1-33.

(Continued)

*Primary Examiner* — James H Alstrum Acevedo
*Assistant Examiner* — Randall L Beane
(74) *Attorney, Agent, or Firm* — Quarles & Brady LLP; Gavin J. Milczarek-Desai

(57) ABSTRACT

The present invention provides polypeptides, compositions thereof, and methods for use of the polypeptides in treating bacterial infection and for use as disinfectants.

27 Claims, 5 Drawing Sheets

(56) References Cited

OTHER PUBLICATIONS

Gupta et al., (2011). "Engineering a Synthetic Ligand for Tumor Necrosis Factor—Alpha." Bioconj. Chem. 22: 1473-1478.

Betanzos et al., (2009). "Bacterial Glycoprofiling by Using Random Sequence Peptide Microarrays." ChemBioChem 10: 877-888.

Domenyuk et al., (2013). "A Technology for Developing Synbodies with Antibacterial Activity." PLoS One 8(1): e54162.

Svarovsky et al., (2011). "High-Throughout Platform for Rapid Deployment of Antimicrobial Agents." ACS Comb. Sci. 13: 634-638.

Williams et al., (2009). "Creating Protein Affinity Reagents by Combining Peptide Ligands on Synthetic DNA Scaffolds." J. Am. Chem. Soc. 131: 17233-17241.

* cited by examiner

SEQUENCE LISTING

```
<160> NUMBER OF SEQ ID NOS: 51

<210> SEQ ID NO 1
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is R, K, d-K, l, F, or P
<220> FEATURE:
<221> NAME/KEY: MISC_FEATURE
<222> LOCATION: (2)..(2)
<223> OTHER INFORMATION: X is W, L or R
<220> FEATURE:
<221> NAME/KEY: MISC_FEATURE
<222> LOCATION: (4)..(4)
<223> OTHER INFORMATION: X is R or F
<220> FEATURE:
<221> NAME/KEY: MISC_FEATURE
<222> LOCATION: (5)..(5)
<223> OTHER INFORMATION: X is H, A, N, I, M, F, W, or P
<220> FEATURE:
<221> NAME/KEY: MISC_FEATURE
<222> LOCATION: (6)..(6)
<223> OTHER INFORMATION: X is K, R, G, H, I, L, F, or V
<220> FEATURE:
<221> NAME/KEY: MISC_FEATURE
<222> LOCATION: (7)..(7)
<223> OTHER INFORMATION: X is H, R, K, d-K, Y, A, W, or V
<220> FEATURE:
<221> NAME/KEY: MISC_FEATURE
<222> LOCATION: (8)..(8)
```

```
<223> OTHER INFORMATION: X is F, L, K, M, or P
<220> FEATURE:
<221> NAME/KEY: MISC_FEATURE
<222> LOCATION: (9)..(9)
<223> OTHER INFORMATION: X is K or R
<220> FEATURE:
<221> NAME/KEY: MISC_FEATURE
<222> LOCATION: (11)..(11)
<223> OTHER INFORMATION: X is P, R, D, M, or F
<220> FEATURE:
<221> NAME/KEY: MISC_FEATURE
<222> LOCATION: (12)..(12)
<223> OTHER INFORMATION: X is H, R, or Y
<220> FEATURE:
<221> NAME/KEY: MISC_FEATURE
<222> LOCATION: (15)..(15)
<223> OTHER INFORMATION: X is H, T, or V
<220> FEATURE:
<221> NAME/KEY: MISC_FEATURE
<222> LOCATION: (16)..(16)
<223> OTHER INFORMATION: X is K or F
<220> FEATURE:
<221> NAME/KEY: MISC_FEATURE
<222> LOCATION: (17)..(17)
<223> OTHER INFORMATION: X is R, K, or F

<400> SEQUENCE: 1

Xaa Xaa Arg Xaa Xaa Xaa Xaa Xaa Xaa Arg Xaa Xaa Arg Lys Xaa Xaa
1               5                   10                  15

Xaa

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Asp Arg Ile Phe His Lys Met Gln His Lys Pro Tyr Lys Ile Lys Lys
1               5                   10                  15

Arg

<210> SEQ ID NO 3
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X is R, K, d-K, L, F, or P
<220> FEATURE:
<221> NAME/KEY: MISC_FEATURE
<222> LOCATION: (2)..(2)
<223> OTHER INFORMATION: X is W, L or R
<220> FEATURE:
<221> NAME/KEY: MISC_FEATURE
<222> LOCATION: (5)..(5)
<223> OTHER INFORMATION: X is H, A, N, I, or P
<220> FEATURE:
<221> NAME/KEY: MISC_FEATURE
<222> LOCATION: (7)..(7)
<223> OTHER INFORMATION: X is H, R, K, d-K, Y, or V
<220> FEATURE:
<221> NAME/KEY: MISC_FEATURE
<222> LOCATION: (8)..(7)
<223> OTHER INFORMATION: X is F, L, K, M, or P
<220> FEATURE:
<221> NAME/KEY: misc_feature
<222> LOCATION: (8)..(8)
<223> OTHER INFORMATION: Xaa can be any naturally occurring amino acid
```

```
<220> FEATURE:
<221> NAME/KEY: MISC_FEATURE
<222> LOCATION: (9)..(9)
<223> OTHER INFORMATION: X is K or R
<220> FEATURE:
<221> NAME/KEY: MISC_FEATURE
<222> LOCATION: (12)..(12)
<223> OTHER INFORMATION: X is H or Y
<220> FEATURE:
<221> NAME/KEY: MISC_FEATURE
<222> LOCATION: (15)..(15)
<223> OTHER INFORMATION: X is H, T or V
<220> FEATURE:
<221> NAME/KEY: MISC_FEATURE
<222> LOCATION: (16)..(16)
<223> OTHER INFORMATION: X is K or F
<220> FEATURE:
<221> NAME/KEY: MISC_FEATURE
<222> LOCATION: (17)..(17)
<223> OTHER INFORMATION: X is R, K or F

<400> SEQUENCE: 3

Xaa Xaa Arg Arg Xaa Lys Xaa Xaa Xaa Arg Pro Xaa Arg Lys Xaa Xaa
1               5                   10                  15

Xaa

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Arg Trp Arg Arg His Lys His Phe Lys Arg Pro His Arg Lys His Lys
1               5                   10                  15

Arg

<210> SEQ ID NO 5
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: X is W or R
<220> FEATURE:
<221> NAME/KEY: MISC_FEATURE
<222> LOCATION: (4)..(4)
<223> OTHER INFORMATION: X is R or F
<220> FEATURE:
<221> NAME/KEY: MISC_FEATURE
<222> LOCATION: (5)..(5)
<223> OTHER INFORMATION: X is H, M, F, or W
<220> FEATURE:
<221> NAME/KEY: MISC_FEATURE
<222> LOCATION: (6)..(6)
<223> OTHER INFORMATION: X is K, R, G, H, I, L, F, or V
<220> FEATURE:
<221> NAME/KEY: MISC_FEATURE
<222> LOCATION: (7)..(7)
<223> OTHER INFORMATION: X is H, R, Y, A, or W
<220> FEATURE:
<221> NAME/KEY: MISC_FEATURE
<222> LOCATION: (11)..(11)
<223> OTHER INFORMATION: X is P, R, D, M, or F
<220> FEATURE:
<221> NAME/KEY: MISC_FEATURE
<222> LOCATION: (12)..(12)
<223> OTHER INFORMATION: X is H or R
```

```
<400> SEQUENCE: 5

Arg Xaa Arg Xaa Xaa Xaa Xaa Phe Lys Arg Xaa Xaa Arg Lys His Lys
1               5                   10                  15

Arg

<210> SEQ ID NO 6
<211> LENGTH: 20
<212> TYPE: PRT
<213> ORGANISM: Artificial Sequence
<220> FEATURE:
<223> OTHER INFORMATION: Synthetic

<400> SEQUENCE: 6

Arg Trp Arg Arg His Lys His Phe Lys Arg Pro His Arg Lys His Lys
1               5                   10                  15

Arg Gly Ser Cys
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic

<400> SEQUENCE: 7

Asp Arg Ile Phe His Lys Met Gln His Lys Pro Tyr Lys Ile Lys Lys
1               5                   10                  15

Arg Gly Ser Cys
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (18)..(20)
<223> OTHER INFORMATION: are optionally absent

<400> SEQUENCE: 8

Asp Arg Ile Phe His Lys Met Gln His Lys Pro Tyr Lys Ile Lys Lys
1               5                   10                  15

Arg Gly Ser Cys
            20

<210> SEQ ID NO 9
<211> LENGTH: 44
<212> TYPE: PRT
<213> ORGANISM: Artificial Sequence
<220> FEATURE:
<223> OTHER INFORMATION: Synthetic

<400> SEQUENCE: 9

Asp Arg Ile Phe His Lys Met Gln His Lys Pro Tyr Lys Ile Lys Lys
1               5                   10                  15

Arg Gly Ser Gly Gly Gly Lys Arg Trp Arg Arg His Lys His Phe Lys
            20                  25                  30

Arg Pro His Arg Lys His Lys Arg Gly Ser Gly Cys
        35                  40
```

```
<210> SEQ ID NO 10
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: d-K

<400> SEQUENCE: 10

Lys Trp Arg Arg His Lys His Phe Lys Arg Pro His Arg Lys His Lys
1               5                   10                  15

Arg

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Leu Trp Arg Arg His Lys His Phe Lys Arg Pro His Arg Lys His Lys
1               5                   10                  15

Arg

<210> SEQ ID NO 12
<211> LENGTH: 17
<212> TYPE: PRT
<213> ORGANISM: Artificial Sequence
<220> FEATURE:
<223> OTHER INFORMATION: Synthetic

<400> SEQUENCE: 12

Phe Trp Arg Arg His Lys His Phe Lys Arg Pro His Arg Lys His Lys
1               5                   10                  15

Arg

<210> SEQ ID NO 13
<211> LENGTH: 17
<212> TYPE: PRT
<213> ORGANISM: Artificial Sequence
<220> FEATURE:
<223> OTHER INFORMATION: Synthetic

<400> SEQUENCE: 13

Pro Trp Arg Arg His Lys His Phe Lys Arg Pro His Arg Lys His Lys
1               5                   10                  15

Arg

<210> SEQ ID NO 14
<211> LENGTH: 17
<212> TYPE: PRT
<213> ORGANISM: Artificial Sequence
<220> FEATURE:
<223> OTHER INFORMATION: Synthetic

<400> SEQUENCE: 14

Arg Arg Arg Arg His Lys His Phe Lys Arg Pro His Arg Lys His Lys
1               5                   10                  15

Arg
```

```
<210> SEQ ID NO 15
<211> LENGTH: 17
<212> TYPE: PRT
<213> ORGANISM: Artificial Sequence
<220> FEATURE:
<223> OTHER INFORMATION: Synthetic

<400> SEQUENCE: 15

Arg Leu Arg Arg His Lys His Phe Lys Arg Pro His Arg Lys His Lys
1               5                   10                  15

Arg

<210> SEQ ID NO 16
<211> LENGTH: 17
<212> TYPE: PRT
<213> ORGANISM: Artificial Sequence
<220> FEATURE:
<223> OTHER INFORMATION: Synthetic

<400> SEQUENCE: 16

Arg Trp Arg Arg Ala Lys His Phe Lys Arg Pro His Arg Lys His Lys
1               5                   10                  15

Arg

<210> SEQ ID NO 17
<211> LENGTH: 17
<212> TYPE: PRT
<213> ORGANISM: Artificial Sequence
<220> FEATURE:
<223> OTHER INFORMATION: Synthetic

<400> SEQUENCE: 17

Arg Trp Arg Arg Asn Lys His Phe Lys Arg Pro His Arg Lys His Lys
1               5                   10                  15

Arg

<210> SEQ ID NO 18
<211> LENGTH: 17
<212> TYPE: PRT
<213> ORGANISM: Artificial Sequence
<220> FEATURE:
<223> OTHER INFORMATION: Synthetic

<400> SEQUENCE: 18

Arg Trp Arg Arg Ile Lys His Phe Lys Arg Pro His Arg Lys His Lys
1               5                   10                  15

Arg

<210> SEQ ID NO 19
<211> LENGTH: 16
<212> TYPE: PRT
<213> ORGANISM: Artificial Sequence
<220> FEATURE:
<223> OTHER INFORMATION: Synthetic

<400> SEQUENCE: 19

Arg Trp Arg Arg Pro Lys His Phe Lys Arg Pro His Arg Lys His Lys
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 20

Arg Trp Arg Arg His Lys Arg Phe Lys Arg Pro His Arg Lys His Lys
1               5                   10                  15

Arg

<210> SEQ ID NO 21
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(7)
<223> OTHER INFORMATION: d-K

<400> SEQUENCE: 21

Arg Trp Arg Arg His Lys Lys Phe Lys Arg Pro His Arg Lys His Lys
1               5                   10                  15

Arg

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Arg Trp Arg Arg His Lys Tyr Phe Lys Arg Pro His Arg Lys His Lys
1               5                   10                  15

Arg

<210> SEQ ID NO 23
<211> LENGTH: 17
<212> TYPE: PRT
<213> ORGANISM: Artificial Sequence
<220> FEATURE:
<223> OTHER INFORMATION: Synthetic

<400> SEQUENCE: 23

Arg Trp Arg Arg His Lys Val Phe Lys Arg Pro His Arg Lys His Lys
1               5                   10                  15

Arg

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Arg Trp Arg Arg His Lys His Leu Lys Arg Pro His Arg Lys His Lys
1               5                   10                  15

Arg

<210> SEQ ID NO 25
<211> LENGTH: 17
<212> TYPE: PRT
<213> ORGANISM: Artificial Sequence
<220> FEATURE:
<223> OTHER INFORMATION: Synthetic
```

<400> SEQUENCE: 25

Arg Trp Arg Arg His Lys His Lys Lys Arg Pro His Arg Lys His Lys
1               5                   10                  15

Arg

<210> SEQ ID NO 26
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: d-K

<400> SEQUENCE: 26

Arg Trp Arg Arg His Lys His Met Lys Arg Pro His Arg Lys His Lys
1               5                   10                  15

Arg

<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Arg Trp Arg Arg His Lys His Pro Lys Arg Pro His Arg Lys His Lys
1               5                   10                  15

Arg

<210> SEQ ID NO 28
<211> LENGTH: 17
<212> TYPE: PRT
<213> ORGANISM: Artificial Sequence
<220> FEATURE:
<223> OTHER INFORMATION: Synthetic

<400> SEQUENCE: 28

Arg Trp Arg Arg His Lys His Phe Arg Arg Pro His Arg Lys His Lys
1               5                   10                  15

Arg

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Arg Trp Arg Arg His Lys His Phe Lys Arg Pro Tyr Arg Lys His Lys
1               5                   10                  15

Arg

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Arg Trp Arg Arg His Lys His Phe Lys Arg Pro His Arg Lys Thr Lys
1               5                   10                  15

Arg

<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Arg Trp Arg Arg His Lys His Phe Lys Arg Pro His Arg Lys Val Lys
1               5                   10                  15

Arg

<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

Arg Trp Arg Arg His Lys His Phe Lys Arg Pro His Arg Lys His Phe
1               5                   10                  15

Arg

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Arg Trp Arg Arg His Lys His Phe Lys Arg Pro His Arg Lys His Lys
1               5                   10                  15

Lys

<210> SEQ ID NO 34
<211> LENGTH: 17
<212> TYPE: PRT
<213> ORGANISM: Artificial Sequence
<220> FEATURE:
<223> OTHER INFORMATION: Synthetic

<400> SEQUENCE: 34

Arg Trp Arg Arg His Lys His Phe Lys Arg Pro His Arg Lys His Lys
1               5                   10                  15

Phe

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Arg Trp Arg Phe His Lys His Phe Lys Arg Pro His Arg Lys His Lys

```
1               5                   10                  15
Arg

<210> SEQ ID NO 36
<211> LENGTH: 17
<212> TYPE: PRT
<213> ORGANISM: Artificial Sequence
<220> FEATURE:
<223> OTHER INFORMATION: Synthetic

<400> SEQUENCE: 36

Arg Trp Arg Arg Met Lys His Phe Lys Arg Pro His Arg Lys His Lys
1               5                   10                  15

Arg

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Arg Trp Arg Arg Phe Lys His Phe Lys Arg Pro His Arg Lys His Lys
1               5                   10                  15

Arg

<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Arg Trp Arg Arg Trp Lys His Phe Lys Arg Pro His Arg Lys His Lys
1               5                   10                  15

Arg

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Arg Trp Arg Arg His Arg His Phe Lys Arg Pro His Arg Lys His Lys
1               5                   10                  15

Arg

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Arg Trp Arg Arg His Gly His Phe Lys Arg Pro His Arg Lys His Lys
1               5                   10                  15

Arg
```

<210> SEQ ID NO 41
<211> LENGTH: 17
<212> TYPE: PRT
<213> ORGANISM: Artificial Sequence
<220> FEATURE:
<223> OTHER INFORMATION: Synthetic

<400> SEQUENCE: 41

Arg Trp Arg Arg His His His Phe Lys Arg Pro His Arg Lys His Lys
1               5                   10                  15

Arg

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Arg Trp Arg Arg His Ile His Phe Lys Arg Pro His Arg Lys His Lys
1               5                   10                  15

Arg

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Arg Trp Arg Arg His Leu His Phe Lys Arg Pro His Arg Lys His Lys
1               5                   10                  15

Arg

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Arg Trp Arg Arg His Phe His Phe Lys Arg Pro His Arg Lys His Lys
1               5                   10                  15

Arg

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Arg Trp Arg Arg His Val His Phe Lys Arg Pro His Arg Lys His Lys
1               5                   10                  15

Arg

<210> SEQ ID NO 46
<211> LENGTH: 17
<212> TYPE: PRT

```
<213> ORGANISM: Artificial Sequence
<220> FEATURE:
<223> OTHER INFORMATION: Synthetic

<400> SEQUENCE: 46

Arg Trp Arg Arg His Lys Ala Phe Lys Arg Pro His Arg Lys His Lys
1               5                   10                  15

Arg

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Arg Trp Arg Arg His Lys Trp Phe Lys Arg Pro His Arg Lys His Lys
1               5                   10                  15

Arg

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Arg Trp Arg Arg His Lys His Phe Lys Arg Arg His Arg Lys His Lys
1               5                   10                  15

Arg

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Arg Trp Arg Arg His Lys His Phe Lys Arg Asp His Arg Lys His Lys
1               5                   10                  15

Arg

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Arg Trp Arg Arg His Lys His Phe Lys Arg Met His Arg Lys His Lys
1               5                   10                  15

Arg

<210> SEQ ID NO 51
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 51

Arg Trp Arg Arg His Lys His Phe Lys Arg Phe His Arg Lys His Lys
1               5                   10                  15
Arg
```

US 9,309,298 B2

ANTI-BACTERIAL POLYPEPTIDES AND PATHOGEN SPECIFIC SYNTHETIC ANTIBODIES

CROSS-REFERENCE

This Application is a 371 application of PCT/US2012/063029 filed Nov. 1, 2012, which claims priority to U.S. Provisional Patent Application Ser. No. 61/554,593 filed Nov. 2, 2011, incorporated by reference herein in their entirety.

STATEMENT OF U.S. GOVERNMENT INTEREST

This work was funded by grant number W911NF-10-1-0299 awarded by the Defense Advanced research Projects Agency. The U.S. government has certain rights in the invention.

BACKGROUND

Antimicrobial resistance of bacteria is rapidly increasing and has been declared a multinational public health crisis. Thus, there is a need for a new generation of therapeutics which are (i) less prone to development of resistance in microbes and (ii) more specific to the target(s) of interest. Natural antimicrobial peptides (AP) are well known as a part of the innate immune system and have been extensively studied. Despite the overall enthusiasm, since 1945 there were just a few commercial products based on AP and for topical use only. The majority of AP based research and development has been limited to naturally occurring AP's or their derivatives. In turn, natural AP's are evolutionary optimized to be toxic and share a broad mechanism of action. The present invention overcomes these limitations in the art.

SUMMARY OF THE INVENTION

In a first aspect, the present invention provides isolated polypeptides comprising an amino acid sequence according to the formula
R1-R2-R3-R4-R5-R6-R7-R8-R9-R10-R11-R12-R13-R14-R15-R16-R17 (SEQ ID NO: 1), wherein R1 is selected from the group consisting of R, K, d-K, L, F, and P;

R2 is selected from the group consisting of W, L, and R;

R3 is R;

R4 is selected from the group consisting of R and F;

R5 is selected from the group consisting of H, A, N, I, M, F, W, and P;

R6 is selected from the group consisting of K, R, G, I, L, F, and V;

R7 is selected from the group consisting of H, R, K, d-K, Y, A, W, and V;

R8 is selected from the group consisting of F, L, K, M, and P;

R9 is selected from the group consisting of K and R;

R10 is R;

R11 is selected from the group consisting of P, R, D, M, and F;

R12 is selected from the group consisting of H, R and Y;

R13 is R;

R14 is K;

R15 is selected from the group consisting of H, T, and V;

R16 is selected from the group consisting of K and F; and

R17 is selected from the group consisting of R, K, and F.

In a second aspect, the present invention provides isolated nucleic acids encoding the polypeptide of any embodiment of the first aspect of the invention. In a third aspect, the present invention provides recombinant expression vectors comprising the isolated nucleic acid of the second aspect of the invention operatively linked to a promoter. In a fourth aspect, the present invention provides recombinant host cells, comprising the expression vector of claim 8.

In another aspect, the invention provides pharmaceutical compositions, comprising an isolated polypeptide of any embodiment of the first aspect of the invention and a pharmaceutically acceptable carrier. In a sixth aspect, the invention provides compositions, comprising an isolated polypeptide of any embodiment of the first aspect of the invention linked to a targeting moiety, including but not limited to compounds capable of targeting the composition to a bacterial cell.

In a further aspect, the invention provides biomedical devices, wherein the biomedical device comprises one or more polypeptides or compositions of any embodiment of the invention disposed on and/or in the biomedical device. In another aspect, the present invention provides anti-bacterial compositions comprising one or more polypeptides or compositions of any embodiment of the invention.

In a further aspect, the invention provides methods for treating a bacterial infection, comprising administering to a subject in need thereof an amount effective to treat the infection of one or more polypeptides, compositions, or biomedical devices of any embodiment the invention. In another aspect, the invention provides methods for disinfecting a surface, comprising contacting the surface with one or more polypeptides or compositions of any embodiment of the invention.

In a further aspect, the present invention provides isolated peptides, comprising the amino acid sequence DRIFHKM-QHKPYKIKKR (SEQ ID NO: 2), or a functional equivalent thereof, as well as isolated nucleic acids encoding the peptide, recombinant expression vectors comprising the isolated nucleic acids operatively liked to a promoter; and recombinant host cells comprising the recombinant expression vector. In another aspect, the invention provides compositions, comprising DRIFHKMQHKPYKIKKR (SEQ ID NO: 2), or a functional equivalent thereof linked to a cell death moiety, wherein the cell death moiety is capable of killing bacterial cells. In a still further aspect, the invention provides compositions, comprising DRIFHKMQHKPYKIKKR (SEQ ID NO: 2), or a functional equivalent thereof, linked to a P. aeruginosa cell binding domain. The invention further provides methods for using DRIFHKMQHKPYKIKKR (SEQ ID NO: 2), or a functional equivalent thereof, or compositions thereof, for treating bacterial infections or disinfecting a surface.

"B" in the presence of single peptide RW; E) "B" in the presence of single peptide DR. Concentration of RW, DR and DR-RW is 25 uM.

Figure 5:
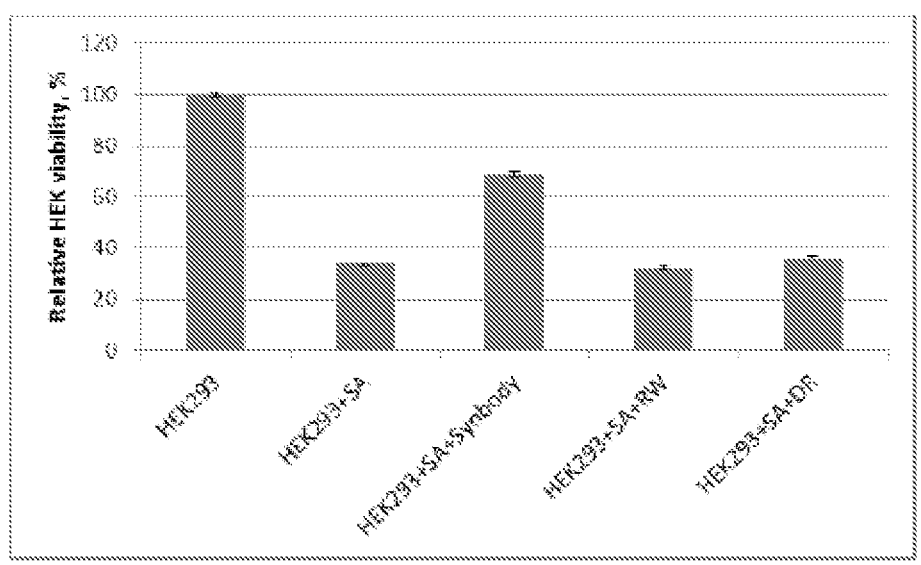

FIG. 5. Protective effect of synbody DR-RW an HEK 293 cells in co-culture with *Staphylococcus aureus*.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique* $2^{nd}$ *Ed*. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tryosine (Tyr; Y), and valine (Val; V).

All embodiments within and between different aspects of the invention can be combined unless the context clearly dictates otherwise.

In a first aspect, the present invention provides isolated polypeptide comprising an amino acid sequence according to the formula

R1-R2-R3-R4-R5-R6-R7-R8-R9-R10-R11-R12-R13-R14-R15-R16-R17 (SEQ ID NO: 1), wherein
R1-R2-R3-R4-R5-R6-R7-R8-R9-R10-R11-R12-R13-R14-R15-R16-R17 (SEQ ID NO: 1), wherein
R1 is selected from the group consisting of R, K, d-K, L F, and P;
R2 is selected from the group consisting of W, L, and R;
R3 is R;
R4 is selected from the group consisting of R and F;
R5 is selected from the group consisting of H, A, N, I, M, F, W, and P;
R6 is selected from the group consisting of K, R, G, H, I, L, F, and V;
R7 is selected from the group consisting of H, R, K, d-K, Y, A, W, and V;
R8 is selected from the group consisting of F, L, K, M, and P;
R9 is selected from the group consisting of K and R;
R10 is R;
R11 is selected from the group consisting of P, R, D, M, and F;
R12 is selected from the group consisting of H, R and Y;
R13 is R;
R14 is K;
R15 is selected from the group consisting of H, T, and V;
R16 is selected from the group consisting of K and F; and
R17 is selected from the group consisting of R, K, and F.

As disclosed in the examples that follow, the inventors have discovered that the polypeptides according to the invention exhibit potent, broad spectrum anti-bacterial activity and thus can be used, for example, in methods to treat bacterial infection or as anti-bacterial compositions. The polypeptides are non-toxic below 100 uM to human cells in vitro, and do not generate an immune response or acute toxicity in vivo in mice.

In one embodiment, the isolated polypeptide comprises an amino acid sequence according to the formula

R1-R2-R3-R4-R5-R6-R7-R8-R9-R10-R11-R12-R13-R14-R15-R16-R17 (SEQ ID NO: 3), wherein
R1 is selected from the group consisting of R, K, d-K, L, F, and P;
R2 is selected from the group consisting of W, L, and R;
R3 is R;
R4 is R;
R5 is selected from the group consisting of H, A, N, I, and P;
R6 is K;
R7 is selected from the group consisting of H, R, K, d-K, Y, and V;
R8 is selected from the group consisting of F, L, K, M, and P;
R9 is selected from the group consisting of K and R;
R10 is R;
R11 is P;
R12 is selected from the group consisting of H and Y;
R13 is R;
R14 is K;
R15 is selected from the group consisting of H, T, and V;
R16 is selected from the group consisting of K and F; and
R17 is selected from the group consisting of R, K, and F.

In this embodiment, it is further preferred that R2 is R, R5 is P, and/or R7 is R.

In a preferred embodiment, a polypeptide according to this embodiment includes at least 1 amino acid difference (1, 2, 3, 4, 5, or more changes) from the polypeptide RWRRHKH-FKRPHRKHKR (SEQ ID NO: 4). As demonstrated in the examples that follow, polypeptides according to this embodiment show improved activity against *Staphylococcus aureus* compared to the originally identified RWRRHKH-FKRPHRKHKR (SEQ ID NO: 4) polypeptide.

In another embodiment, the isolated polypeptide comprises an amino acid sequence according to the formula

R1-R2-R3-R4-R5-R6-R7-R8-R9-R10-R11-R12-R13-R14-R15-R16-R17 (SEQ ID NO: 5), wherein
R1 is R;
R2 is selected from the group consisting of W and R;
R3 is R;
R4 is selected from the group consisting of R and F;
R5 is selected from the group consisting of H, M, F, and W;
R6 is selected from the group consisting of K, R, G, H, I, L, F, and V;
R7 is selected from the group consisting of H, R, Y, A, and W;
R8 is F;
R9 is K;
R10 is R;

R11 is selected from the group consisting of P, R, D, M, and F;

R12 is selected from the group consisting of H and R;

R13 is R;

R14 is K;

R15 is H;

R16 is K; and

R17 is R.

In this embodiment, it is further preferred that R6 is either I or F.

In a preferred embodiment, a polypeptide according to this embodiment includes at least 1 amino acid difference (1, 2, 3, 4, 5, or more changes) from the polypeptide RWRRHKH-FKRPHRKHKR (SEQ ID NO: 4). As demonstrated in the examples that follow, polypeptides according to this embodiment show improved activity against *Pseudomonas aeruginosa* compared to the originally identified RWRRHKH-FKRPHRKHKR (SEQ ID NO: 4) polypeptide.

In a further embodiment, the isolated peptides comprise an amino acid sequence selected form SEQ ID NOS: 4, 10-51 (Table 1 and 2 peptides).

In all of these embodiments, the isolated polypeptides may comprise or consist of the recited amino acid sequence. For polypeptides comprising the recited amino acid sequence, the polypeptide can be of any suitable length. In one non-limiting embodiment the isolated polypeptides are 17-50 amino acids in length; in other embodiments 17-45, 17-40, 17-35, 17-30, 17-25, or 17-20 amino acids in length. As will be apparent to those of skill in the art, the polypeptides may comprise additional amino acids as are appropriate for a given purpose. For example, additional amino acid residues may be added to link the polypeptides of the invention to another domain to provide for a composition of interest. In one non-limiting example, as disclosed below, the polypeptides of the invention were linked to a bacterial binding polypeptide; in this example, the polypeptides are immobilized to a microarray using an C-terminal amino acid tail, in this case GSC, while certain constructs described herein comprise a GSG tail. Thus, in another embodiment of any of the above embodiments, the isolated polypeptides may further comprise a C-terminal tail, such as a 1-5 amino acid tail (ie: 1-5, 1-4, 1-3, 1-2, 2-5, 2-4, 2-3, 3-5, 3-4, 4-5, 1, 2, 3, 4, or 5 amino acid C-terminal tail). In one embodiment, the C-terminal tail comprises GSC or GSG.

Similarly, the polypeptides may be otherwise modified in any suitable way to provide desired properties, such as increased half-life when administered in vivo. In a non-limiting embodiment, the covalent attachment of polymers, especially polyethylene glycol (PEG), has been used to protect certain proteins from enzymatic hydrolysis in the body and thus prolong half-life. The amino acids may comprise D amino acids, L amino acids, or a combination of D and L amino acids as is deemed most suitable for a given use.

As used herein, the polypeptide are "isolated", meaning that they are at least partially purified from other polypeptides and contaminating materials (such as gel and chromatography materials used to isolated the polypeptides). The polypeptides can be made by any suitable technique, including but not limited to recombinant DNA technology and standard polypeptide synthetic techniques.

The polypeptides may be in solution, or present on a solid surface for uses disclosed herein. The polypeptides may also be stored in any suitable state, including but not limited to frozen or lyophilized.

In a second aspect, the present invention provides isolated nucleic acid encoding the polypeptide of embodiment or combination of embodiments of the invention. The isolated nucleic acids can be used, for example, for recombinant production of the polypeptides of the invention. The isolated nucleic acid sequence may comprise RNA or DNA. As used herein "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags export signals, and secretory signals, nuclear localization signals, and plasma membrane localization signals. It will be apparent to those of skill in the art, based on the teachings herein, what nucleic acid sequences will encode the polypeptides of the invention.

In a third aspect, the present invention provides recombinant expression vectors comprising the isolated nucleic acid of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The construction of expression vectors for use in transfecting prokaryotic and eukaryotic cells is well known in the art, and thus can be accomplished via standard techniques. (See, for example, Sambrook, Fritsch, and Maniatis, in Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fourth aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique, 2nd Ed*. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In a fifth aspect, the present invention provides pharmaceutical compositions, comprising one or more polypeptides of the invention and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer.

The polypeptides may be the sole active agent in the pharmaceutical composition, or the composition may further comprise one or more other active agents or carrier moieties suitable for an intended use.

In one embodiment, the invention provides compositions, comprising an isolated polypeptide of the invention linked to a targeting moiety. In this embodiment, the polypeptide is covalently linked to a moiety that is capable of targeting the polypeptide to a target of interest. Any suitable targeting moiety can be used, including but not limited to transduction domains, antibodies, or other molecules (nucleic acid aptamers, polypeptides, etc.) that bind to a target of interest. In a preferred embodiment, the targeting moiety comprises a compound capable of targeting the composition to a bacterial cell, as the polypeptides have shown potent anti-bacterial activity.

In one example, the targeting moiety is a polypeptide with an amino acid sequence comprising DRIFHKMQHKPYKIKKRGSC (SEQ ID NO: 7), or a functional equivalent thereof. As demonstrated in the examples that follow, the compositions of this embodiment are particularly useful, for example, as anti-bacterials and in methods for treating bacterial infection against, for example, S. aureus and P. aeruginosa. The DRIFHKMQHKPYKIKKRGSC (SEQ ID NO: 7) peptide ("DR peptide") reacts with S. aureus and P. aeruginosa, thus providing desirable specificity to the anti-bacterial activity of the isolated polypeptides of the invention. Such a composition can be viewed as a synthetic antibody ("synbody"). As also shown in the examples that follow, the synbodies of the invention demonstrate improved anti-microbial activity (against S. aureus and P. aeruginosa) compared to the anti-bacterial polypeptides alone (which has broad spectrum anti-microbial activity), which makes it less prone to create an antibiotic-resistant strain. Finally, the synbodies of the invention are shown herein to be non-toxic to human cells in vitro, and to not generate an immune response or acute toxicity in vivo in mice. C Functional equivalents of the targeting polypeptides can be identified using techniques such as those disclosed in WO/2008/048970. Far targeting polypeptides comprising the recited amino acid sequence, the polypeptide can be of any suitable length. In one non-limiting embodiment, the targeting polypeptides are 17-50 amino acids in length; in other embodiments, 17-45, 17-40, 17-35, 17-30, 17-25, or 17-20 amino acids in length.

In another embodiment that can be combined with any of the above embodiments, the isolated polypeptide and the targeting moiety are covalently bound via a linker. Any suitable linker capable of chemically linking the targeting moiety and the anti-bacterial polypeptide can be used. The linker may be of any type, including but not limited to an amino acid-based scaffold and a poly-ethylene glycol linker. The scaffold can be rigid or flexible. For example, it was recently shown that when using 20 mer peptides, several different peptide linkers can be used to produce synbodies with similar binding affinities for TNFA (Gupta, et al., Bioconj Chem (2011) doi: 10.1021/bc200091c). In one embodiment, the linker comprises an amino acid scaffold. In another preferred embodiment, the composition comprises the structure (SEQ ID NO: 9)

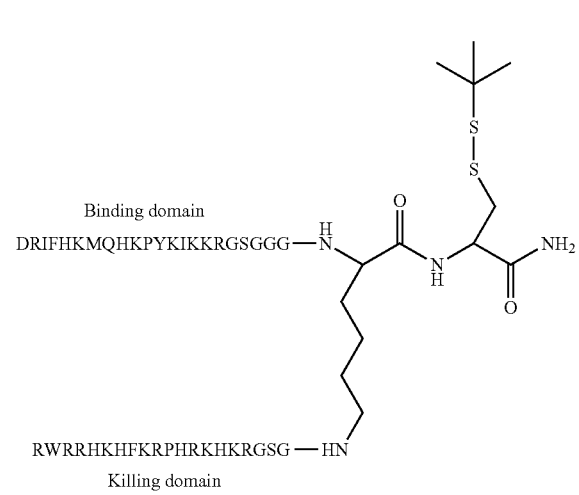

Binding domain
DRIFHKMQHKPYKIKKRGSGGG —

RWRRHKHFKRPHRKHKRGSG — HN
Killing domain

In this embodiment, the anti-bacterial polypeptide ("killing domain") and the binding domain polypeptide include a 3 amino acid tail (i.e.: GSG or GGG), to help provide the space between peptides and scaffold to avoid the steric hindrance and interference in interactions with bacterial cells.

The composition and pharmaceutical compositions can be formulated for administration/use via any suitable route, including but not limited to orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques a intraperitoneally. In preferred embodiments, the compositions are formulated for administration/use as a topical cream, a suspension, an oral formulation, or an intravenous formulation.

In a sixth aspect, the present invention provides biomedical devices, wherein the biomedical devices comprise one or more isolated polypeptides, compositions or pharmaceutical compositions of the invention, disposed on and/or in the biomedical device. Any biomedical device that is subject to bacterial infection, particularly S. aureus and/or P. aeruginosa infection is contemplated as being within the scope of the invention. In various non-limiting embodiments, the biomedical device can be a medical implant including but not limited to orthopedic implants (such as fracture-fixation devices, joint prostheses (knee, hip shoulder, etc.), etc.), stents, grafts, shunts, stent grafts, angioplasty devices, vascular catheters, urinary catheters, aortic grafts, balloon catheters, fistulas, wound dressings, dental implants, contact lens sterilization solutions, and any implantable drug delivery device. The compositions can present on the biomedical devices in any suitable amount or arrangement, and may be combined with one or more other components. In one embodiment, the compositions are added together with a polymer coating.

In a seventh aspect, the present invention provides an anti-bacterial composition comprising one or more isolated polypeptides, compositions or pharmaceutical compositions of the invention. In various non-limiting embodiments, the anti-bacterial compositions can be solid (ex: solid soaps) or liquid (ex: liquid soaps), and may be disposed on a substrate (ex: disinfectant wipes).

In an eighth aspect, the present invention provides methods for treating a bacterial infection, comprising administering to subject in need thereof an amount effective to treat the infection of one or more isolated polypeptides, compositions or pharmaceutical compositions, or biomedical device of any embodiment, or combination of embodiments, of the invention. Any subject with a bacterial infection can be treated using the methods of the invention. In a preferred embodiment, the subject is suffering from S. aureus and/or P. aeruginosa infection.

As used herein, "treating" means accomplishing one or more of the following: (a) reducing or eliminating infection in the subject; (b) reducing the severity of one or more symptoms of bacterial infection; (c) limiting or preventing development of one or more symptoms of bacterial infection; (d) inhibiting worsening of one or more symptom of bacterial infection; and (e) limiting or preventing recurrence of one or more symptoms of bacterial infection in subjects that were previously symptomatic for the relevant symptom.

In a ninth aspect, the present invention provides methods for disinfecting a surface, comprising contacting the surface with an anti-bacterial composition of any embodiment of the invention. Any suitable surface can be disinfected, including but not limited to counters, sinks, toilets, door handles, desks, medical tools (such as in hospitals, appliances, furniture, beds, etc. In a preferred embodiment, the methods serve to disinfect against the presence of S. aureus and/or P. aeruginosa.

In a tenth aspect, the present invention provides an isolated peptide, comprising the amino acid sequence DRFIHKMQHKPYKIKKR(GSC) (SEQ ID NO: 8) (wherein the GSC moiety is optional), or a functional equivalent thereof. Peptides according to this aspect of the invention can be used, for example, to target an anti-bacterial compound to S. aureus, and can be used as lytic polypeptides against P. aeruginosa. Functional equivalents of the targeting polypeptides can be identified using techniques such as those disclosed in WO2008/048970. For targeting polypeptides comprising the recited amino acid sequence, the polypeptide can be of any suitable length. In one non-limiting embodiment, the targeting polypeptides are 17-50 amino acids in length in other embodiments, 17-45, 17-40, 17-35, 17-30, 17-25, or 17-20 amino acids in length. All definitions and embodiments of polypeptides and modifications thereto discussed herein apply equally to this aspect of the invention.

In an eleventh aspect, the invention provides isolated nucleic acids encoding the DRFIHKMQHKPYKIKKR (GSC) (SEQ ID NO: 8) polypeptide, or a functional equivalent thereof. All definitions and embodiments of isolated nucleic acids discussed herein apply equally to this aspect of the invention. It will be apparent to those of skill in the art, based on the teachings herein, what nucleic acid sequences will encode the polypeptides of this aspect invention.

In a twelfth aspect, the invention provides recombinant expression vectors comprising the isolated nucleic acid the eleventh aspect of the invention operatively linked to a promoter. All definitions and embodiments of expression vectors discussed herein apply equally to this aspect of the invention.

In a thirteenth aspect, the present invention provides recombinant host cells, comprising the expression vector of the twelfth aspect of the invention. All definitions and embodiments of host cells discussed herein apply equally to this aspect of the invention.

In a fourteenth aspect, the present invention provides compositions, comprising a polypeptide comprising the amino acid sequence DRIFHKMQHKPYKIKKR(GSC) (SEQ ID NO: 8), or a functional equivalent thereof, linked to a cell death moiety, wherein the cell death moiety is capable of killing bacterial cells. In this aspect, the cell death moiety may be any anti-bacterial compound, and preferably one that is capable of killing S. aureus. The cell death moiety may be any type of molecule, such as a nucleic acid, and antibiotic, or a polypeptide. In a preferred embodiment, the cell death moiety comprises a polypeptide, such as an isolated polypeptide of the present invention, particularly the first aspect of the invention. In a further preferred embodiment, the isolated polypeptide and the cell death moiety are covalently bound via a linker, such as disclosed above for the synbodies of the invention. In another embodiment, the invention provides compositions, comprising a polypeptide comprising the amino acid sequence DRIFHKMQHKPYKIKKR(GSC) (SEQ ID NO: 8), or a functional equivalent thereof, linked to a cell binding domain for P. aeruginosa. As noted above, the DRIFHKM-QHKPYKIKKR(GSC) (SEQ ID NO: 8) can be used as a lytic polypeptide against P. aeruginosa, and thus its linkage to a cell binding domain for P. aeruginosa provides enhanced specificity of activity against P. aeruginosa.

In a fifteenth aspect, the present invention provides pharmaceutical compositions, comprising the composition of the fourteenth aspect of the invention, and a pharmaceutically acceptable carrier. All definitions and embodiment of pharmaceutical compositions disclosed herein apply equally to this aspect. In one embodiment, the composition is selected from the group consisting of a topical cream, a suspension, an oral formulation, and an intravenous formulation.

In a sixteenth aspect, the present invention provides biomedical devices, wherein the biomedical device comprises a composition of the fourteenth or fifteenth aspects of the invention disposed on and/or in the biomedical device. All embodiments of biomedical devices disclosed herein apply equally to this aspect.

In a seventeenth aspect, the present invention provides anti-bacterial compositions comprising a composition of the fourteenth or fifteenth aspects of the invention. All embodiments of anti-bacterial compositions disclosed herein apply equally to this aspect.

In an eighteenth aspect, the present invention provides methods for treating a bacterial infection, comprising administering to a subject in need thereof an amount effective to treat the infection of a composition of the fourteenth or fifteenth aspects of the invention, or the biomedical device of the sixteenth aspect of the invention. All embodiments of methods for treating bacterial infection disclosed herein apply equally to this aspect of the invention. In a preferred embodiment, the subject is suffering from a S. aureus and/or P. aeruginosa infection.

In a nineteenth aspect, the invention provides methods for disinfecting a surface, comprising contacting the surface with the anti-bacterial composition the seventeenth aspect of the invention. All embodiments of methods for disinfecting a surface disclosed herein apply equally to this aspect.

EXAMPLES

We have developed a system for screening pathogens simultaneously an 10,000 random sequence peptides to select peptides that specifically target a bacterium as well as peptides that exhibit antimicrobial activity. We then link these peptides to make synbodies with increased reactivity and specificity.

In this way we have designed a new compound that consisted of an antimicrobial peptide with broad spectra of action and specific peptide-binder for *S. aureus*.

(SEQ ID NO: 9)
DRIFHKMQHKPYKIKKRGSGGGK-(RWRRHKHFKRPHRKHKRGSG)C

Molecular Weight: 5431
Net charge at pH 7.0: 17.5
Iso-electric point, pI: 12.4
Average hydrophilicity: 0.9
Ratio hydrophilic residues/total number of residues: 50%

Figure 1:
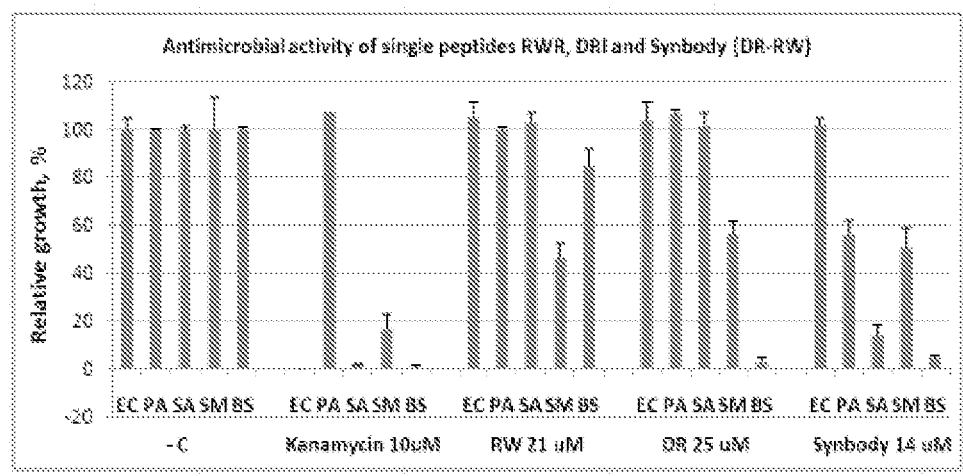
FIG. 1. Graph of results from a solution inhibition assay, which showed increased specificity and activity of a composition of the invention against *S. aureus* compared to pathogenic *E. coli* O111:B4, *P. aeruginosa*, *S. mutans*, and *B. subtilis*.

Solution inhibition assays showed increased specificity and activity of the synbody against *S. aureus* compared to pathogenic *E. coli* O111:B4, *P. aeruginosa*, *S. mutans*, and *B. subtilis*. See FIG. 1. The advantage of the synbody "DR-RW" over the single peptides can be noticed in the range 10-25 uM. Specific activity was increased more than 80% for *S. aureus* and 50% for *P. aeruginosa* but not for other strains.

Minimal inhibition concentrations of the original peptides and synbody were determined and are shown in Table 1.

TABLE 1

| Compound | Avg MIC* (µM) ± SD Strains | | | | |
|---|---|---|---|---|---|
| | EC | PA | SA | SM | BS |
| RWRRHKHFKR PHRKHKRGSC (SEQ. ID NO: 6) | NP | 27 ± 2.3 | 28 ± 1.5 | >100 | 20 ± 0.3 |
| DRIFHKMQHK PYKIKKRGSC (SEQ ID NO: 7) | B | >100 | B | >100 | NP |
| Synbody | >100 | 22 ± 1.8 | 14 ± 0.8 | >100 | 14 ± 1.1 |

Figure 2:
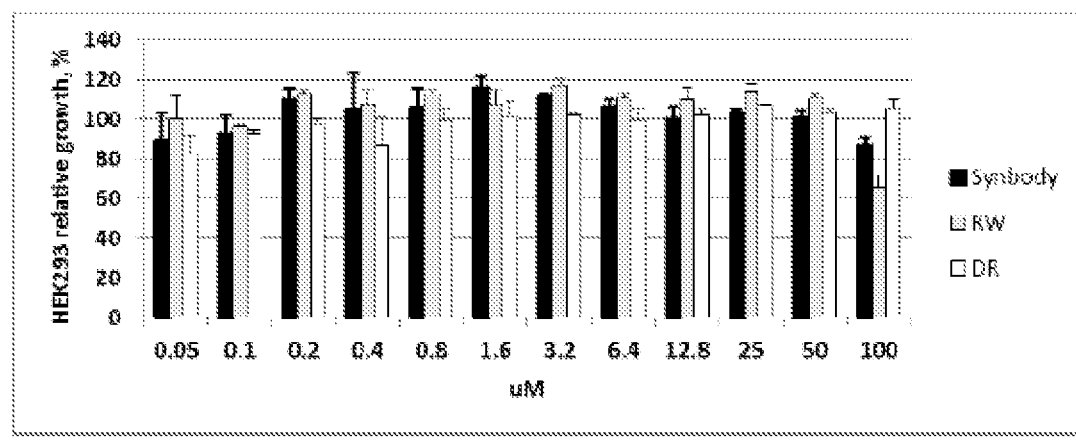
FIG. 2. Graph of cytoxicity data of a composition of the invention in human tissue culture studies.
Figure 3:
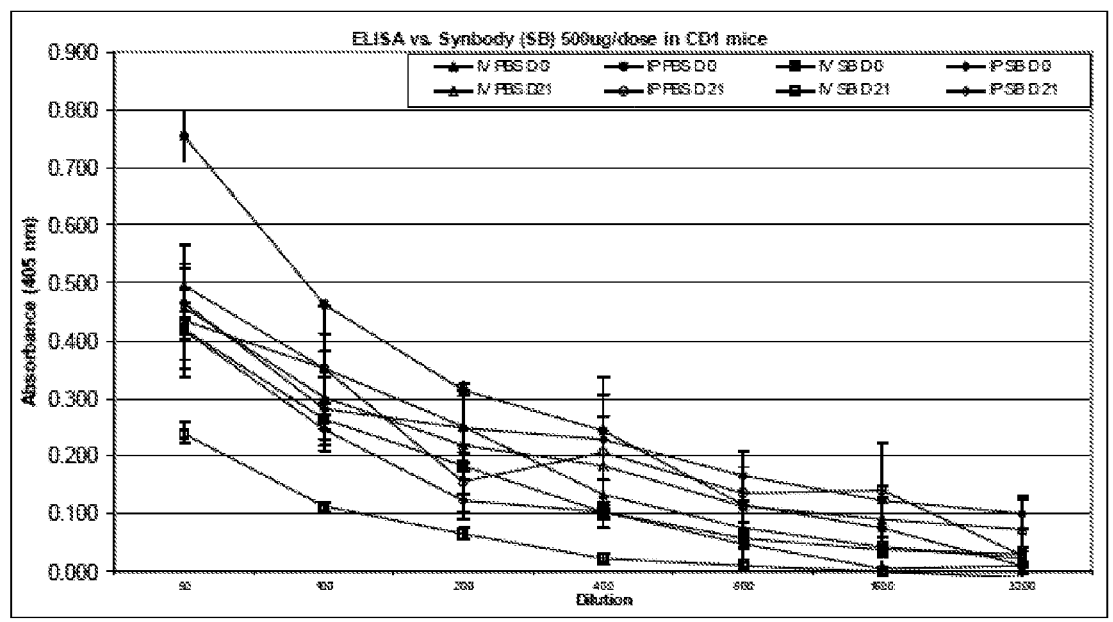
FIG. 3. Graph of immune response cytoxicity data of a composition of the invention in CD1 mice.

*MICs represent averages of at least three independent experiments with standard deviations
NP—no array profile B—peptide binder, no antimicrobial activity Human tissue culture test showed no cytotoxic activity of the new compound in 24 and 48 hours. At the highest concentration of RW and DR-RW (100 uM) there was a slight growth suppression. See FIG. 2. GAL80 synbody was used as a negative control with no activity against *S. aureus*. In vivo characterization of the new compound showed no immune response or acute toxicity at 500 ug dose. See FIG. 3. There was no difference detected in the level of IgG in PBS and synbody injected mice. Synbody was abbreviated as "SB".

Figure 4:
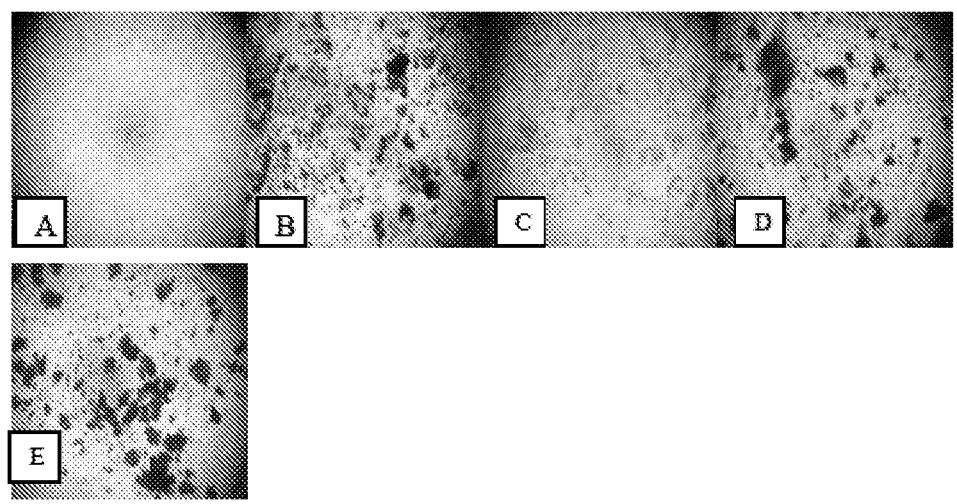
FIG. 4. Protective effect of synbody DR-RW on HEK cells in co-culture with *Staphylococcus aureus*. Light microscopy (10×). A) Negative control—HEK293 only; B) Co-culture of HEK293 and *S. aureus*; C) "B" in the presence of synbody; D)

Test of the synbody in a co-culture of HEK293 cells (Human Embryonic Kidney) (average $2.5*10^4$ cells/vial) with *S. aureus* (average number of cells $4*10^5$) showed protective effect of synbody on human cells. See FIG. 4. Concentration of RW, DR and DR-RW was 25 uM. Additionally, co-culture protective effect of the new compound was demonstrated quantitatively in cell viability assay by measuring cellular ATP content (ATPLight luminescence assay). See FIG. 5.

Mutant Polypeptide Generation

A library of 340 mutants of original lytic peptide (killing domain in synbody) was synthesized with single amino acid substitutions. Mutants along with original peptide as positive control were tested in vitro for inhibition activity against *S. aureus* and *Pseudomonas aeruginosa*. Table 2 shows the sequences of mutants which appeared to be stronger inhibitors than original lytic peptide considering the relative growth of pathogens after 18 hours of co-incubation. Ratio reflect the improvement in activity as "Mutant$_{[Relative\ growth]}$/Orignal$_{[Relative\ growth]}$.

TABLE 2

Mutants with improved activity against *Staphylococcus aureus* compared to the original sequence

| NAME | SEQUENCE | ratio |
|---|---|---|
| Original | RWRRHKHFKRPHRKHKR (SEQ ID NO: 4) | |
| Mut 5 | d-KWRRHKHFKRPHRKHKR (SEQ ID NO: 10) | 1.307927304 |
| Mut 11 | LWRRHKHFKRPHRKHKR (SEQ ID NO: 11) | 1.580014531 |
| Mut 14 | FWRRHKHFKRPHRKHKR (SEQ ID NO: 12) | 1.653121907 |
| Mut 15 | PWRRHKHFKRPHRKHKR (SEQ ID NO: 13) | 1.657818277 |
| Mut 22 | RRRRHKHFKRPHRKHKR (SEQ ID NO: 14) | 6.099847038 |
| Mut 31 | RLRRHKHFKRPHRKHKR (SEQ ID NO: 15) | 1.63307472 |
| Mut 81 | RWRRAKHFKRPHRKHKR (SEQ ID NO: 16) | 1.524734818 |
| Mut 83 | RWRRNKHFKRPHRKHKR (SEQ ID NO: 17) | 13.1518494 |
| Mut 90 | RWRRIKHFKRPHRKHKR (SEQ ID NO: 18) | 1.747091979 |
| Mut 95 | RWRRPKHFKRPHRKHKR (SEQ ID NO: 19) | 9.077177865 |
| Mut 122 | RWRRHKRFKRPHRKHKR (SEQ ID NO: 20) | 17.45233537 |
| Mut 125 | RWRRHKd-KFKRPHRKHKR (SEQ ID NO: 21) | 1.593455872 |
| Mut 139 | RWRRHKYFKRPHRKHKR (SEQ ID NO: 22) | 2.135918634 |
| Mut 140 | RWRRHKVFKRPHRKHKR (SEQ ID NO: 23) | 1.658066056 |
| Mut 151 | RWRRHKHLKRPHRKHKR (SEQ ID NO: 24) | 1.311528986 |
| Mut 152 | RWRRHKHKKRPHRKHKR (SEQ ID NO: 25) | 2.049478319 |
| Mut 153 | RWRRHKHMKRPHRKHKR (SEQ ID NO: 26) | 2.292552667 |
| Mut 155 | RWRRHKHPKRPHRKHKR (SEQ ID NO: 27) | 2.358593278 |
| Mut 162 | RWRRHKHFRRPHRKHKR (SEQ ID NO: 28) | 2.125357849 |
| Mut 239 | RWRRHKHFKRPYRKHKR (SEQ ID NO: 29) | 2.120470588 |
| Mut 297 | RWRRHKHFKRPHRKTKR (SEQ ID NO: 30) | 2.339409643 |

TABLE 2-continued

Mutants with improved activity against *Staphylococcus aureus* compared to the original sequence

| NAME | SEQUENCE | ratio |
|---|---|---|
| Mut 300 | RWRRHKHFKRPHRKVKR (SEQ ID NO: 31) | 1.452775308 |
| Mut 314 | RWRRHKHFKRPHRKHFR (SEQ ID NO: 32) | 1.496984869 |
| Mut 332 | RWRRHKHFKRPHRKHKK (SEQ ID NO: 33) | 2.437812233 |
| Mut 334 | RWRRHKHFKRPHRKHKF (SEQ ID NO: 34) | 2.37037621 |

TABLE 3

Mutants with improved activity against *Pseudomonas aeruginosa* compared to the original sequence.

| NAME | SEQUENCE | ratio |
|---|---|---|
| Original | RWRRHKHFKRPHRKHKR (SEQ ID NO: 4) | |
| Mut 22 | RRRRHKHFKRPHRKHKR (SEQ ID NO: 14) | 2.073068 |
| Mut 74 | RWRFHKHFKRPHRKHKR (SEQ ID NO: 35) | 1.01715 |
| Mut 93 | RWRRMKHFKRPHRKHKR (SEQ ID NO: 36) | 1.035459 |
| Mut 94 | RWRRFKHFKRPHRKHKR (SEQ ID NO: 37) | 1.210653 |
| Mut 98 | RWRRWKHFKRPHRKHKR (SEQ ID NO: 38) | 1.182732 |
| Mut 102 | RWRRHRHFKRPHRKHKR (SEQ ID NO: 39) | 1.076808 |
| Mut 108 | RWRRHGHFKRPHRKHKR (SEQ ID NO: 40) | 1.191053 |
| Mut 109 | RWRRHHHFKRPHRKHKR (SEQ ID NO: 41) | 1.39484 |
| Mut 110 | RWRRHIHFKRPHRKHKR (SEQ ID NO: 42) | 4.386687 |
| Mut 111 | RWRRHLHFKRPHRKHKR (SEQ ID NO: 43) | 1.709515 |
| Mut 114 | RWRRHFHFKRPHRKHKR (SEQ ID NO: 44) | 10.95044 |
| Mut 120 | RWRRHVHFKRPHRKHKR (SEQ ID NO: 45) | 3.684 |
| Mut 121 | RWRRHKAFKRPHRKHKR (SEQ ID NO: 46) | 2.296826 |
| Mut 122 | RWRRHKRFKRPHRKHKR (SEQ ID NO: 20) | 3.121367 |
| Mut 138 | RWRRHKWFKRPHRKHKR (SEQ ID NO: 47) | 1.315058 |
| Mut 139 | RWRRHKYFKRPHRKHKR (SEQ ID NO: 22) | 1.163654 |
| Mut 202 | RWRRHKHFKRRHRKHKR (SEQ ID NO: 48) | 1.3565 |
| Mut 204 | RWRRHKHFKRDHRKHKR (SEQ ID NO: 49) | 2.107394 |
| Mut 213 | RWRRHKHFKRMHRKHKR (SEQ ID NO: 50) | 1.185178 |
| Mut 214 | RWRRHKHFKRFHRKHKR (SEQ ID NO: 51) | 1.133627 |

We claim:

1. A composition, comprising an isolated polypeptide linked to a targeting moiety, wherein the targeting moiety is a polypeptide with an amino acid sequence comprising DRIFHKMQHKPYKIKKR (SEQ ID NO: 2).

2. The composition of claim 1, wherein the isolated polypeptide and the targeting moiety are covalently bound via a linker.

3. The composition of claim 2, wherein the linker comprises an amino acid scaffold.

4. The composition of claim 3, wherein the composition comprises SEQ ID NO: 9.

5. A pharmaceutical composition, comprising the composition of claim 1, and a pharmaceutically acceptable carrier.

6. The pharmaceutical composition of claim 5, wherein the composition is selected from the group consisting of a topical cream, a suspension, an oral formulation, and an intravenous formulation.

7. A biomedical device, wherein the biomedical device comprises compositions according to claim 1 disposed on or in the biomedical device.

8. An anti-bacterial composition comprising compositions according to claim 1.

9. A method for treating a bacterial infection, comprising administering to a subject in need thereof an amount effective to treat the infection a composition according to any one of claims 1-6, or the biomedical device of claim 7.

10. The method of claim 9, wherein the subject is suffering from a *S. aureus* and/or *P. aeruginosa* infection.

11. A method for disinfecting a surface, comprising contacting the surface with the anti-bacterial composition of claim 8.

12. An isolated peptide, comprising the amino acid sequence DRIFHKMQHKPYKIKKR (SEQ ID NO: 2).

13. An isolated nucleic acid encoding the polypeptide of claim 12.

14. A recombinant expression vector comprising the isolated nucleic acid of claim 13 operatively linked to a promoter.

15. A recombinant host cell, comprising the expression vector of claim 14.

16. A composition, comprising an isolated polypeptide according to claim 12 linked to a cell death moiety, wherein the cell death moiety is capable of killing bacterial cells.

17. The composition of claim 16, wherein the cell death moiety is capable of killing *S. aureus*.

18. The composition of claim 16, wherein the cell death moiety comprises a polypeptide.

19. The composition of claim 16 wherein the isolated polypeptide and the cell death moiety are covalently bound via a linker.

20. A composition, comprising an isolated polypeptide according to claim 12 linked to a *P. aeruginosa* cell binding domain.

21. A pharmaceutical composition, comprising the composition of claim 16, and a pharmaceutically acceptable carrier.

22. The pharmaceutical composition of claim 21, wherein the composition is selected from the group consisting of a topical cream, a suspension, an oral formulation, and an intravenous formulation.

23. A biomedical device, wherein the biomedical device comprises a composition according to claim 16 disposed upon the biomedical device.

24. An anti-bacterial composition comprising a composition according to claim 16.

25. A method for treating a bacterial infection, comprising administering to a subject in need thereof an amount effective to treat the infection a composition according to claim 16.

26. The method of claim 25, wherein the subject is suffering from a *S. aureus* and/or *P. aeruginosa* infection.

27. A method for disinfecting a surface, comprising contacting the surface with the anti-bacterial composition of claim 24.

\* \* \* \* \*